United States Patent [19]

Wernicke

[11] Patent Number: 5,454,276
[45] Date of Patent: Oct. 3, 1995

[54] MULTI-DIRECTIONAL MAGNETIC FLUX PIPE INSPECTION APPARATUS AND METHOD

[76] Inventor: Timothy K. Wernicke, 912 Summertree La., Southlake, Tex. 76092

[21] Appl. No.: 100,468

[22] Filed: Jul. 30, 1993

[51] Int. Cl.$^6$ .................................................. G01N 27/82
[52] U.S. Cl. .................. 73/865.8; 73/866.5; 324/220; 324/226
[58] Field of Search .................. 73/865.8, 866.5, 73/623; 324/220, 226, 228

[56] References Cited

U.S. PATENT DOCUMENTS

| | | | |
|---|---|---|---|
| 3,238,448 | 3/1966 | Wood et al. | 324/37 |
| 3,483,466 | 12/1969 | Crouch et al. | 324/220 |
| 3,593,122 | 7/1971 | Barton et al. | 324/220 |
| 3,786,684 | 1/1974 | Wiers et al. | 324/220 |
| 3,810,384 | 5/1974 | Evans | 73/626 |
| 3,906,357 | 9/1975 | Runshang | 324/37 |
| 3,906,358 | 9/1975 | Stone | 324/220 |
| 4,072,894 | 2/1978 | Barton | 324/221 |
| 4,105,972 | 8/1978 | Smith | 324/220 |
| 4,107,605 | 8/1978 | Hudgell | 324/220 |
| 4,310,796 | 1/1982 | Braithwaite et al. | 324/220 |
| 4,370,895 | 2/1983 | Wright | 74/216 |
| 4,439,730 | 3/1984 | Kauffman | 324/232 |
| 4,444,777 | 5/1984 | Sharp et al. | 324/220 |
| 4,458,601 | 7/1984 | Braithwaite et al. | 104/138 G |
| 4,628,613 | 12/1986 | Laymon | 33/544 |
| 4,742,298 | 5/1988 | Ando et al. | 324/220 |
| 4,769,598 | 9/1988 | Krieg et al. | 324/226 |
| 4,789,827 | 12/1988 | Bergander | 324/220 |
| 4,851,773 | 7/1989 | Rothstein | 324/220 |
| 4,952,875 | 8/1990 | Adams et al. | 324/220 |
| 5,068,608 | 11/1991 | Clark, Jr. | 324/220 |
| 5,134,367 | 7/1992 | Griffith et al. | 324/220 |

FOREIGN PATENT DOCUMENTS

| | | | |
|---|---|---|---|
| 108489 | 9/1978 | Japan | 73/623 |
| 43563 | 2/1987 | Japan | 324/220 |
| 218953 | 8/1990 | Japan | 324/220 |
| 1283640 | 1/1987 | U.S.S.R. | 324/220 |

*Primary Examiner*—Hezron E. Williams
*Assistant Examiner*—Daniel S. Larkin
*Attorney, Agent, or Firm*—John W. Montgomery; Ross, Clapp, Korn & Montgomery

[57] ABSTRACT

A pipeline inspection pig includes a drive mechanism, a first field generator and first sensor section connected to the drive mechanism and is driven thereby helically through the pipeline in a clockwise rotational direction. A second field generator and second sensor section is also connected to the drive mechanism and is driven thereby helically through the pipeline in a counterclockwise direction. A data recorder is operatively connected to the first sensor section and to the second sensor section for recording field interruption data from which a plot of anomalies in the pipeline can be generated as a grid of intersecting helical sensor signal pathways of the first and second sensors.

20 Claims, 3 Drawing Sheets

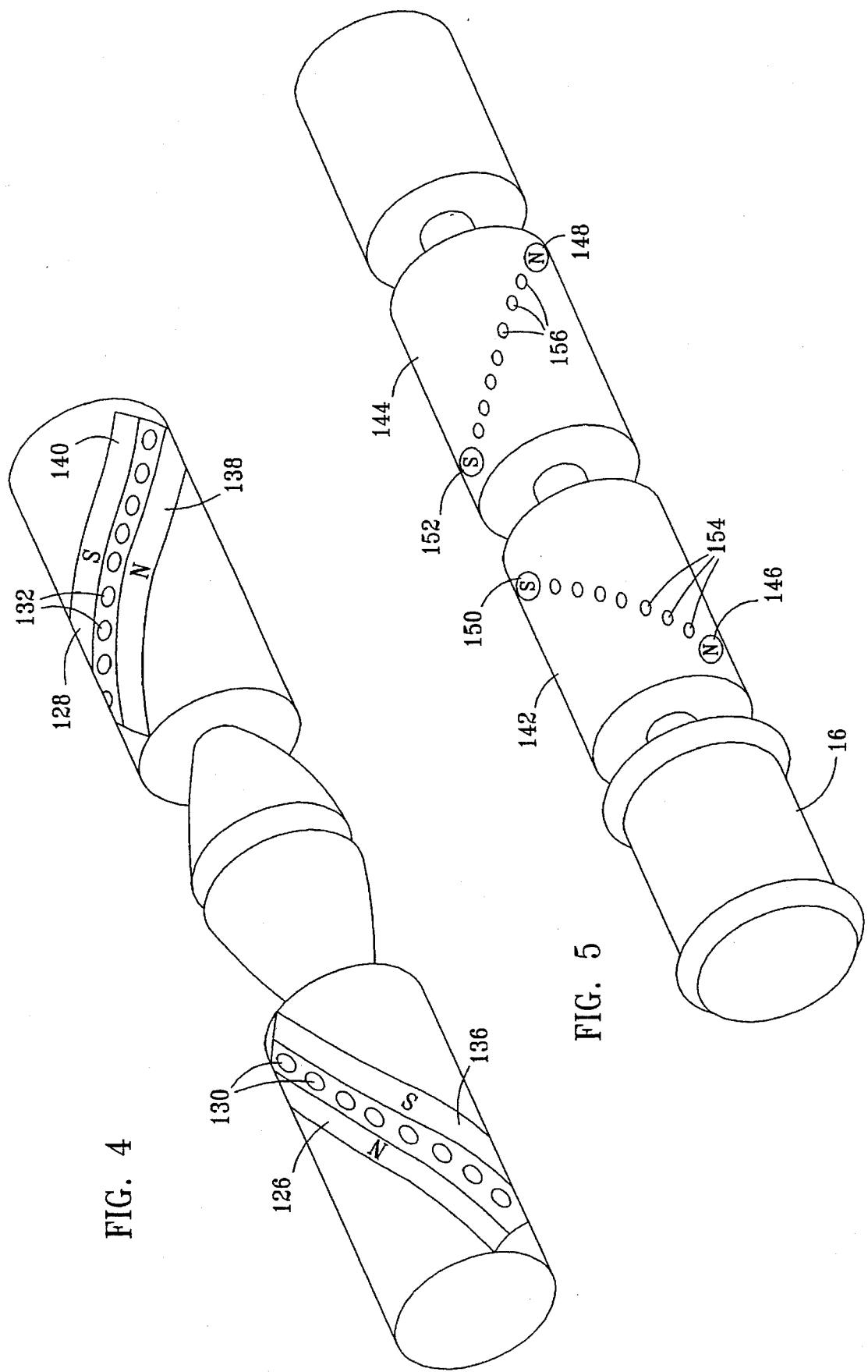

MULTI-DIRECTIONAL MAGNETIC FLUX PIPE INSPECTION APPARATUS AND METHOD

TECHNICAL FIELD OF THE INVENTION

The present invention relates to a pipeline inspection device, and particularly, to an electromagnetic field generator and field interruption or anomaly detection sensor, which is carried by a pig through an existing steel pipeline for on-site inspection.

BACKGROUND OF THE INVENTION

Numerous pipe inspection pigs are in existence and have been used in connection with non-destructive inspection of pipelines for gaseous or liquid materials, such as natural gas, liquid hydrocarbons, or water.

Most underground pipelines are made out of ferromagnetic steel and for that reason, inspection devices such as eddy current detectors, as may be used in inspection of non-ferromagnetic tubing, such as stainless steel or other types of tubing used in heat exchangers and the like are not particularly useful in connection with underground steel pipelines, such as chemical pipelines, liquid hydrocarbon pipelines, gas pipelines, water or sewage pipes, and the like.

Various methods of detecting flaws or defects from the inside of a pipe or pipeline have been attempted with varying degrees of success. Ferromagnetic induction devices have been used as disclosed in U.S. Pat. No. 4,742,298. This invention was directed to determining the presence and the magnitude of surface flaws and to overcoming difficulties encountered in determining the presence and the magnitude of surface flaws in a pipe. The solution proposed was to use a cylindrical primary alternating current coil which is coaxially aligned with the pipe to generate a high frequency AC magnetic field in the pipeline, a multiple cylindrical secondary AC sensing coil where arranged at prescribed intervals in a circumferential direction around the interior of the pipe, each secondary coil having an axis parallel to the axis of the primary coil. The AC voltage sensed at each secondary coil is set to be proportional to the density of a parallel component of magnetic flux caused by the AC magnetic field generator.

Eddy current sensing probes have also been used primarily in connection with non-destructive inspection and testing of relatively thin-walled tubing which is not ferromagnetic material. Such tubing does exist in steam generators and heating exchangers having been the primary focus of eddy current probes as disclosed in U.S. Pat. No. 4,851,773 which discloses a single direction rotating head profilometer. One embodiment of that device discloses an electromechanical eddy current probe having a rotatable sensing head for sensing the wall thickness and for locating local defects in a tube or conduit through which it is passed. Basically, the mechanical profilometer probe was designed to detect dents in the interior surface of steam generator tubes. The position of the rotating head is varied along the length of the tubing being inspected as the probe is drawn through the tubing with a cable.

Another eddy current probe is disclosed in U.S. Pat. No. 4,952,875 in which a plurality of pairs of diametrically opposed sensing coils are alternatingly staggered along the longitudinal axis of the test sensor to give complete coverage of the interior pipe surface and are further permitted to move in and out to accommodate the size differences or constrictions in the pipeline. However, the sensor probe is intended to move longitudinally through the pipeline.

Also, U.S. Pat. No. 5,068,608 discloses multiple coil eddy current probe system and an eddy current probe is disclosed in which a defect is first detected when the probe is positioned adjacent the defect and a series of axially spaced probes are activated to sense and detect the extremities of a crack or other discontinuity. Generally, eddy current probes have not been particularly successful with respect to underground pipelines constructed of steel or other ferromagnetic materials and having pipeline walls with thicknesses substantially greater than the normal eddy current penetration depth. However, one attempt to provide an eddy current probe or ferromagnetic pipeline flaw detection was disclosed in U.S. Pat. No. 4,107,605. There is no indication of the usefulness of such probes in connection with determining longitudinal cracks which are parallel to the direction of movement of the probe assembly.

The most popular and currently most useful sensors for ferromagnetic pipeline inspection have been magnetic flux generators and magnetic flux leakage sensors which are positioned circumferentially around an inspection pig which is moved longitudinally through the pipeline. Examples of such sensors are disclosed in U.S. Pat. Nos. 4,105,972, 4,310,796, 4,444,777 and 4,458,601. The operation of such magnetic flux detection probes is described in U.S. Pat. No. 4,789,827 in connection with a magnetic flux detection probe in which the sensors are intentionally spaced at different radial distances or spaced different distances from the interior pipe surface in an effort to obtain greater accuracy with respect to the location of the flaw or defect on the inside or the outside of the pipe wall.

Some attempts have been made to detect defects at different angular orientations in connection with testing and inspecting pipes as they are being manufactured. U.S. Pat. No. 3,906,357 discloses an exterior pipe testing device in which there are two external sensor sections, one having a plurality of fixed sensing shoes circumferentially spaced around the pipe to be inspected which depends upon linear movement of the pipe therethrough for detecting flaws or defects primarily oriented circumferentially around the pipe. A second inspection unit is provided which has a pair of opposed magnetic sensing shoes which is rotated rapidly around the outside of the pipe to be inspected in an effort to detect longitudinal cracks which might otherwise go unnoticed with the fixed shoe sensing unit. Complex circuitry is used to coordinate the sensor input from each of the sensing units with a rotating magnetic pulse generator geared to the linear motion of the pipe being manufactured. A purpose of this device is to actuate one or more spray cans at the linear and the circumferential position where a manufacturing flaw is detected either by the linear inspection unit or the rotary inspection unit. Application of such a testing device to on-site underground pipelines has not been demonstrated.

Another exterior pipe testing device has been disclosed in U.S. Pat. No. 4,439,730, in which pairs of north and south poles of magnets are held adjacent to the exterior wall of a pipe at uniformly spaced apart positions circumferentially around the pipe. The north and south poles are positioned between the north and south poles of longitudinally spaced apart circular magnets around the pipe. The circumferential spaced apart magnets are rotated at a high rate of speed so that orthogonically directed resultant magnetic field is produced on opposite sides of the pipe between the north and south pole of the rotating magnets. Pairs of flux detectors are interposed on opposite sides of the rotating magnet. The magnets are rotated at a sufficiently high rate of speed relative to the longitudinal motion of the pipe since the flux field interruptions in the same incremental area of the pipe. Again, complex circuitry is required in order to coordinate the sensor input from each of the sensing units because of the high rotational speed (320 revolutions per minute in the example set forth in '730) in order to keep track of the sampled signals from the two overlapping sensors and further, to coordinate them to a longitudinal position along the pipe. At a longitudinal travelling speed of 80 feet per minute as set forth in the example, the device must make four complete revolutions during every one foot of travel, which is consistent with the sensor field slightly over three inches long, so that 100% of the pipe surface can be covered. Such a device is not considered practical for internal inspection of existing underground pipelines. Potentially, the rate of rotation may not be achievable for internal pipe inspection devices.

Pipeline flaw detectors for use inside of existing pipelines have also provided rotary mechanisms for rotating sensing shoes helically through the pipeline as the detector is moved linearly therealong. One such device is disclosed in U.S. Pat. No. 3,238,448 which, upon detecting a flaw, actuates a strong electromagnet to magnetize the corresponding portion of the pipeline so that the position of the defect can be detected from aboveground with magnetic sensors. This device rotates two opposed search units in a single direction such that only very large flaws can be accurately detected and locating any such detected flaws is dependent upon a second careful searching action for the magnetized pipe section from aboveground.

Another pipeline inspection apparatus is disclosed in U.S. Pat. No. 4,072,894 which produces a circumferentially directed magnetic flux field as flux leakage detection sensors are resiliently held against the pipe wall surface and helically moved through the pipe to pass transversely across any longitudinally extending anomalies in the pipe wall. This device produces only a circumferentially directed magnetic flux and helical movement of the sensing probes in only one direction.

One of the most popular and currently the most widely used state-of-the-art internal magnetic flux gas pipe inspection devices comprises a pipeline pig which has sealing cups around the exterior perimeter to both center the apparatus and to drive it by differential gas pressure along the pipeline. A magnetic flux is generated by multiple circumferentially spaced magnets with north and south poles axially spaced apart and a magnetic flux sensor interposed therebetween. In operation, the pig travels linearly through the pipeline and sensory input data from each sensor is recorded as a function of distance of travel. When a defect, void, or other anomaly in the pipe is indicated by sensing an interruption of a smooth longitudinal magnetic flux, then such an anomaly is recorded on a graph as a function of time or distance. A major drawback of this device is that the longitudinal, or axially aligned, magnetic flux cannot always detect longitudinal voids or defects such as a uniform deterioration along a continuous welded seam of the pipeline. Resolution is determined by the size of the multiple sensor unit. A second set of circumferentially positioned magnetic flux generators and flux leakage sensors can be positioned at a small staggered distance with respect to the first set so that the space between the flux generator and sensor shoes is covered by the second set of sensors. Still, minor disturbances at the start of a longitudinal defect and at a distant end of the longitudinal defect may go unnoticed on a graph.

The best resolution available is approximately limited by the size of the gap between the sensors. Often, one or more of the multiple sensors may fail during a run several miles through a pipeline, which may give an entire line of approximately one to three inches wide in which no discontinuities would be detected along the length of the pipe. In order to reduce some of this risk, the pigs are often rotated at up to about a 1° angle, which amounts to about one revolution per 1,000 linear feet. The magnetic flux is still linearly aligned in the axial direction and the small amount of rotation, if any, is so small that longitudinal voids continue to be substantially undetectable.

SUMMARY OF THE INVENTION

The current invention overcomes the problems of the prior art by providing a pig with two flux generator and sensor sections, which sections are counter-rotated as they are moved through the pipeline. The two sections each have one or more flux generators correspondingly interposed with one or more sensors, all of which are angularly oriented to a helical angle caused by simultaneous linear and rotational movement of the sections through the pipeline. Preferably, the two sections of generators and sensors are counter-rotated at opposite angles with equal magnitude. For example, one section rotates at $+\theta°$ and one at $-\theta°$ where $\theta°$ is a constant or fixed helical angle. Thus, the two separate sections spiral in counter-rotational directions uniformly through the pipeline. The angle $\theta$ is selected to allow the pig to move rapidly through the pipeline with substantially complete coverage from both angularly disposed sensor sections. Uniquely, the sensory data from each of the flux generators and sensors can detect discontinuities both longitudinally and circumferentially in the pipe. To increase the sensitivity, a plurality of sensors are used in each section, each sensor positioned circumferentially around each section of the pig so that the entire surface of the pipeline is scanned by at least one sensor of each section as the pig moves through the pipeline. The sensory data from each sensor in one section is coordinated to sensory data from a corresponding sensor in the other section depending on the fixed relative rotation angle. Superimposing the data from all of the sensors for both of the sections produces a grid pattern which is useful to confirm and further define circumferential deterioration, defects, or anomalies as well as longitudinal deterioration, defects, or anomalies. An odometer reading, a graphical time indicator, a direct distance measurements, or another distance indicating mechanism may be superimposed on the grid pattern to confirm synchronization of the grid pattern to accurately specify where any detected feature, defect, deterioration, flaw, or anomaly is physically located along the length of the pipeline. Circumferential positioning of any detected feature around the pipeline is also determinable based upon the relative circumferential location of the particular sensors providing the input data so that cost-effective repairs can be made. Preferably, the sensors are rotated and also the flux is generated at the same helical angle. Advantageously, opposite angles for the two counter-rotating flux generating and sensing units will produce a uniform set of graphs for overlapping depiction of the sensor data, thereby substantially increasing the resolution of the graphical depiction obtained. The data may be recorded separately and later superimposed using computer analysis techniques. Alternatively, an on-board processor computer may simultaneously combine the signals from the two flux generator and sensor units. The input from the odometer may also be combined with the flux generator signals on board.

According to one feature of a preferred embodiment, the rotation of each of the flux generating and sensor units is synchronized with or timed to each other so that precision counter-rotation is accomplished. Both sensor sections may be synchronized to a linear odometer. Alternatively and advantageously, the sections are directly geared to each other to insure synchronization.

A further advantage is provided by the capability of the present inventive device to locate longitudinal pipe seams and lack of homogeneity in the pipeline material. If the seams are found to be aligned in a position corresponding to a particular accelerated corrosion mechanism, then adverse effects on the pipeline might be expected and repair schedules can be correspondingly adjusted. Thus, the repair and/or replacement schedule can be more accurately determined where seam positions are accurately detected during inspection. This is true even where no other flaws, pits, defects, or other anomalies are detected. Alternating seam positions in adjacent pipe section is typical in modern pipelines. Aligned seams could lead to catastrophic failure, such as a propagated eruption along an extended length of pipeline. Thus, detection of faulty installation is important. Also, alignment of the longitudinal seam of any pipe section with a primary or secondary failure mechanism is an important aspect to detect. Applicant's invention provides these capabilities in a fast-moving internal pipe inspection pig.

BRIEF DESCRIPTION OF THE DRAWINGS

The foregoing objects, advantages, and features, as well as other objects and advantages will become more apparent with reference to the description and drawings below, in which like elements represent like numerals and in which:

FIG. 4 is a schematic perspective view of an alternative embodiment of a pipe inspection pig in which each counter-rotating flux generator and sensor section includes a single elongated magnet with a plurality of sensors between north and south poles of flux generating magnets which contact the pipeline; and FIG. 5 is a schematic perspective view of yet another alternative embodiment in which oppositely angled flux fields are created with first and second sets of oppositely angled magnets spaced apart linearly with sensors therebetween to detect anomalies in an overlapping grid pattern.

DETAILED DESCRIPTION OF THE PREFERRED EMBODIMENTS

Figure 1:
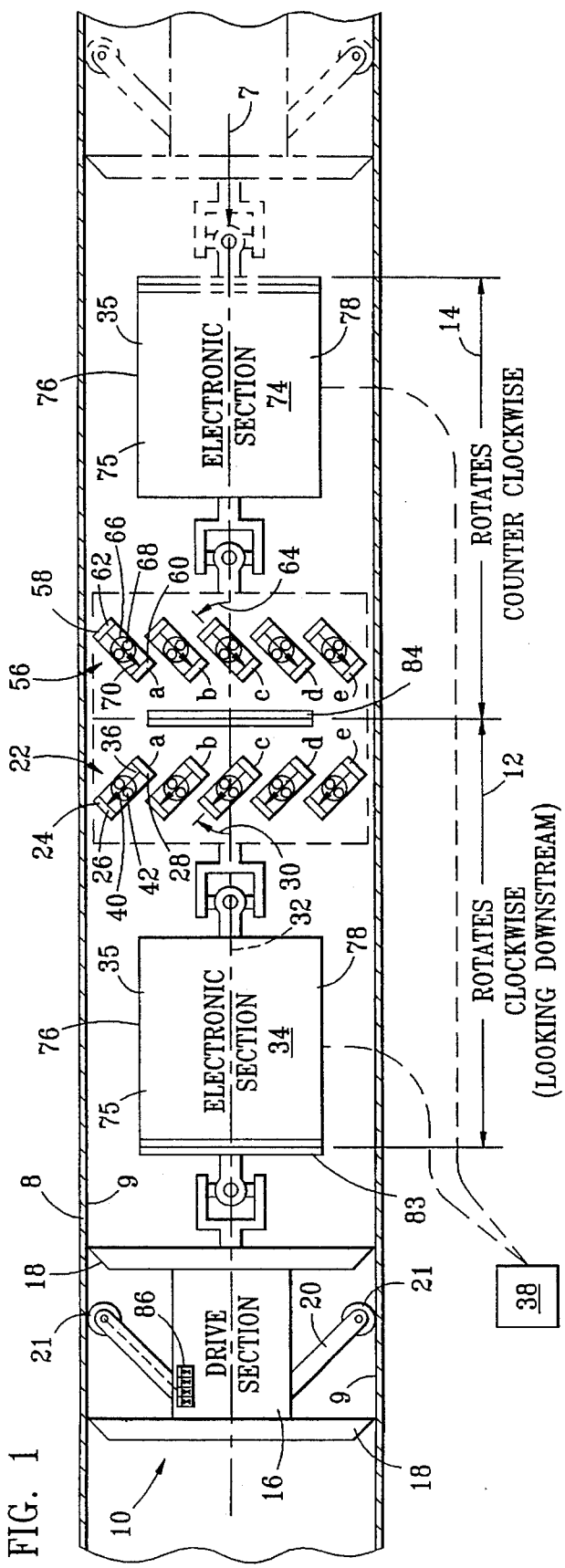
FIG. 1 is a schematic side view depiction of the counter-rotating pipe inspection device of the current invention within a pipeline section.

FIG. 1 is a schematic side view depiction of a counter-rotating pipeline inspection device 10 of the current invention. Inspection device 10 comprises a multi-component pig with a first rotating section 12 and a second counter-rotating section 14 which are driven or pulled by a drive section 16 which may be attached to first rotating section 12 and which may be of the type having one or more flexible cups 18 which engage against an inner wall 9 of a pipeline 8 to drive the inspection device 10 therealong with the stream of fluid 7 being carried within the pipeline 8. Typically, the fluid is a natural gas or a liquid hydrocarbon material so that pipeline inspection can be undertaken with minimum interference to the flow of materials being carried within the pipeline. The drive section 16 may also be provided with a mechanical rolling guide 20, which may comprise a plurality of evenly spaced apart rollers 21 spring-loaded against the interior wall 9 of the pipeline so that the flexible cups 18 are maintained in substantially uniform compression therearound. A similar rear guide section (not shown) may also be connected to second rotating section 14 to more accurately support the tracking end of the device 10.

The first section 12 is provided with one or more magnetic flux generator and magnetic sensor units 22. Each of the flux generator and sensor units 22 comprise a magnet 24 having a north pole pipeline contact 26 and a south pole pipeline contact 28 which are fastened to the first section positioned at an angle 30 relative to the central axis 32 of the pipeline 8. The north and south poles are thus spaced apart and produce a substantially uniform magnetic flux field 36 (schematically depicted as an arrow) between the spaced apart north and south poles within the ferromagnetic wall 9 of pipeline 8. Each of the flux generator and sensor units 22 further include a sensor unit 40 corresponding to each of the generator magnets 24 positioned between the north and south pole contacts 26 and 28 in close proximity of the interior wall 9 of pipeline 8, so that any interruption of the substantially uniform magnetic flux field 36 may be caused by a crack or another anomaly in the ferromagnetic wall 9 of the pipeline 8 at a given location having a component aligned perpendicular to flux field 36 will cause a detectable discontinuity in the flux field which can be detected with sensor unit 40. Each sensor unit 40 may comprise a plurality of individual flux responsive devices 42, such as wire coils, magneto-diodes or Hall effect devices, so that the area between the north and south poles can be further subdivided into identifiable incremental areas. The first section 12 may also include an electronic section 34 by which sensory data from the sensor units 40 is stored, processed, or transmitted to a remote location 38 for storage and/or processing of the data, i.e., a computer at 38. Where the magnetic flux generating units 22 include electromagnets 24, rather than permanent magnets 24, the electronic section 34 may also provide power to the electromagnets 24.

Figure 2:
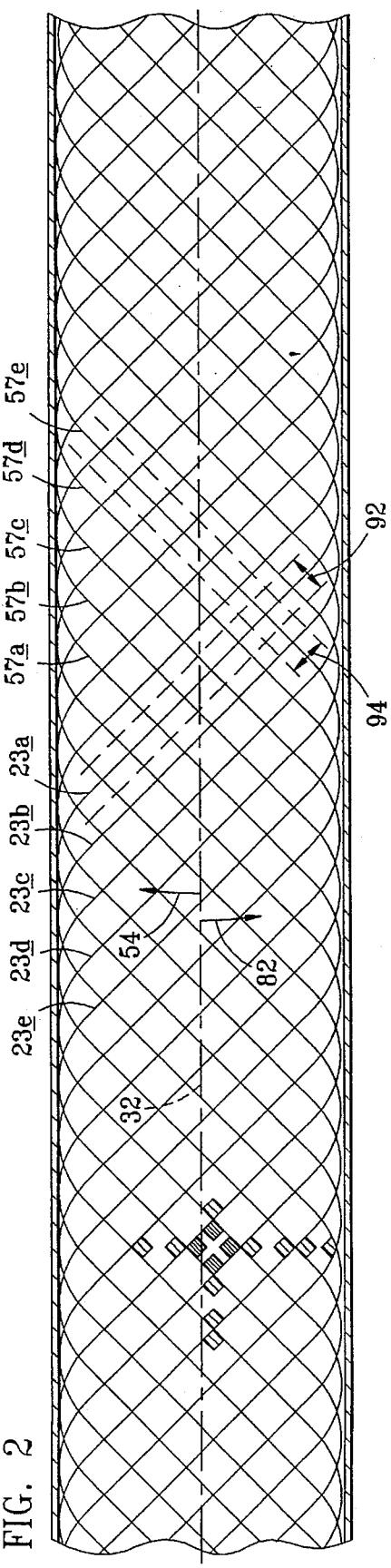
FIG. 2 is a graphical depiction of a grid pattern produced by overlapping sensory data from a plurality of flux generator and flux leakage sensors which are counter-rotated through a pipeline.

In one preferred embodiment as more fully understood with reference to both FIGS. 1 and 2, the first section 12 rotates at a rate corresponding to the linear movement of pig 10 through the pipeline 8 to produce a helical rotational angle 54 which corresponds to the angle 30 between the north pole contact 26 and the south pole contact 28. Preferably, the angle 30 and the corresponding helical rotational angle 54 are chosen to be approximately 45°. Thus, in this preferred embodiment, the pig moves forward a distance approximately equal to its rotation distance. The helical motion, together with a plurality of circumferentially spaced sensor units 40 and 56 on rotating sections 12 and 14, respectively, allows the pig 10 to move through the pipeline 8 creating a grid pattern of flux and detection paths (as shown in FIG. 2) at a substantial rate of speed without requiring excessive high rates of rotation of first rotating section 12, which carries the flux generator and sensor units 22.

The second rotating section 14 also has one or more flux generator and sensor units 56, which each have a flux generator magnet 58 having a north pole contact 60 and south pole contact 62 which are positioned at an angle 64 relative to the pipeline axis 32 oppositely directed from angle 30 of the first section. Each of the flux generator and sensor units 56 includes a second flux sensor unit 66, which may include multiple flux sensor devices 68. Thus, the north and south poles 60 and 62 generate a substantially uniform flux field 70 (shown schematically as an arrow) extending between the north and south poles such that the flux field 70 is at an angle 64 with respect to the pipeline axis 32. Anomalies or interruptions with components aligned perpendicular to the flux field 70 will be detected with flux sensor units 66. The second rotating section 14 also includes a second electronic section 74. The first electronic section 34 and the second electronic section 74 may include an onboard platter at 35, a recorder 75, a processor 76, or a transmitter 78 by which signals or sensory data from the flux sensor units 40 or 66, respectively, may be recorded, processed, as with an onboard platter 35 or transmitted to a remote location 38 with a recorder or processor, such as a computer at 38 at a location aboveground or otherwise remote from the pig. Further, the electronic sections 34 and 74 may provide battery power for operation of the flux generator sensor units. Sufficient electrical power may be provided for a plurality of electromagnets 24 and 58.

Also in the preferred embodiment, as more fully understood, referring to both FIGS. 1 and 2, the second rotating section 14 is rotated at a rate proportional to the longitudinal motion of the pig 10 through the pipeline 8 to produce a helical movement angle 82, which helical angle 82 preferably corresponds to magnet pole position angle 64, which angles 64 and 82 are preferably selected as the opposite of angles 30 (and 54) of the first unit. Further preferably, where angle 30 and 54 is a positive 45° angle, the angle 64 (and 82) is a negative 45° angle relative to the axis 32.

In order to accommodate the counter-rotation of the two sections 12 and 14, they are rotationally coupled to the drive section 16 with a rotational coupling mechanism 83 and to each other with a rotational coupling mechanism 84. The rotation of the first section 12 is coordinated with the rotation of the second section 14 and their longitudinal separation is maintained substantially constant. Thus, by determining the position of the pig 10, as with an odometer 86 in the drive section 16 or elsewhere, or with a linearly rigid axially flexible strand 87 (shown in FIG. 3), the length of which is measurable from an originating point, so that a substantially uniform grid pattern of magnetic flux signals or sensory data can be generated by overlapping the signals or sensory data from the first section 12 with the signals or sensory data 40 from the second section. Each of the first flux sensors 40 and each of second flux sensors 66 provide sensory data. Preferably, there are a plurality of flux sensors 40 and flux sensors 66, each with sensory data signals, which sensory data overlaps to produce a grid pattern which can then be indexed to the pipe position at which the signals are generated. Such a pattern may be produced with a continuous onboard plotter 35 or at an above-ground computer 38 receiving the sensor data signals.

FIG. 2 schematically depicts the overlapping paths of travel for a plurality of counter-rotating units 22 and 56. For example purposes, path lines for each of the plurality of first flux generator and sensor units 22a–e produce corresponding path lines 23a–e in FIG. 2 and each of the second flux generator and sensor units 56a–e generate path lines 57a–e. With the path lines only indicated, it will be understood that signals from sensor units 40a–e will be superimposed on path lines 23a–e in FIG. 2 and the signals corresponding to second sensor units 66a–e will be superimposed on path lines 57a–e in FIG. 2. Where the signals from a sensor unit 40 are produced from a series of incremental sensor units 42, those signals will be correspondingly superimposed at appropriate locations at or adjacent to the path lines 23a–e and will be superimposed on either side of the path lines. This will provide a width 92 for path lines 23a–e and a width 94 for path lines 57a–e.

The magnitude of the signal for each incremental area provided from each incremental sensor unit 42 can be superimposed on the signal for each incremental sensor unit 68 as by printing numeric values on a chart indicating a representative sum or by shading the area with a printer, which shading becomes additive corresponding to the strength of the signal, so that higher numbers or darker areas indicate greater discontinuities in the flux where smaller numbers or lighter areas indicate a lesser degree of discontinuity or indicating that the pipe has structural integrity. Large cracks or discontinuities would be indicated by an aligned series of darkened areas or high numbers. It will be understood by those skilled in the art that color coding might also be used as has been done in the past with respect to detecting defects using longitudinal flux line internal devices or from the exterior of a pipeline using somewhat more complex high rotational speed detectors.

Figure 3:
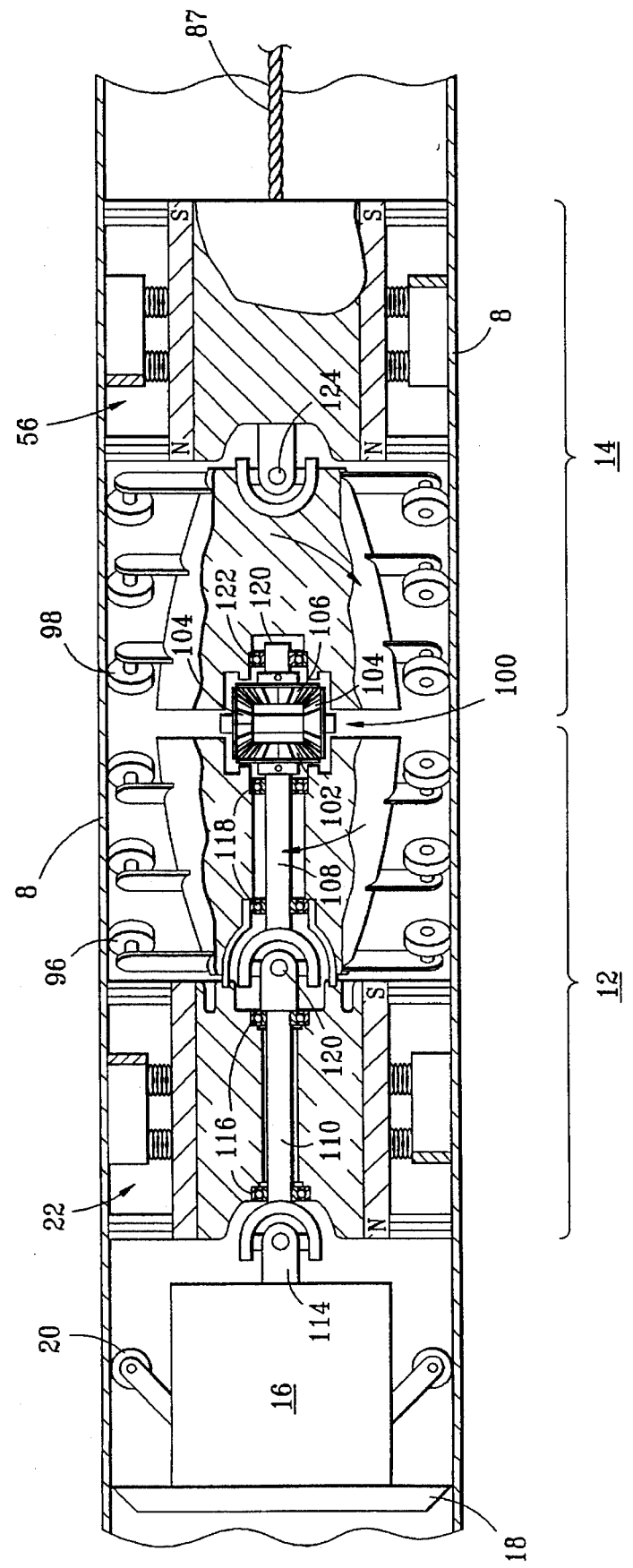
FIG. 3 is a schematic partial cross-sectional view of a magnetic field generator and flux leakage sensor inspection device according to one embodiment of the present invention in which counter-rotating sections are geared for synchronized counter-rotation with each other.

In connection with counter-rotating flux generator and sensor units, and particularly with respect to inspecting long lengths of underground pipeline where access to the pig is limited between insert and exit points, the result of the present invention can be maximized by maintaining the counter-rotational sections in accurate synchronization so that they counter-rotate at the same speed and at opposite angles without deviation along the length of the pipeline being inspected. This synchronization is advantageously maintained with the embodiment of the invention as depicted in FIG. 3 in which the front drive unit is provided with axially aligned guide wheels 20 and each counter-rotating section is provided with angularly disposed guide wheels 96 for the first section and guide wheels 98 for the second section. Guide wheels 96 contact the interior surface 9 of pipeline 8 at an angle θ=+45° relative to axis 32 and guide wheels 98 contact the interior surface of pipeline 8 at an angle θ=−45° with respect to the axis 32.

In order to properly insure one-for-one counter-rotation in one preferred embodiment as shown in FIG. 3, a mechanical gear mechanism 100 interconnects the first section 12 with the second section 14 such that first section 12 is driven, for example, through engagement of bevel gear 102, with idler bevel gears 104 and the second section 14 is driven by being rigidly connected to bevel gear 106 which engages with idler bevel gears 104. The idler gears 104 are maintained in a fixed position relative to the drive section 16 through shaft 108 which is flexibly coupled to shaft 110 as, for example, through a universal joint 112 and shaft 110 is coupled to drive section 16 through U-joint 114. The first section 12 is mounted on shafts 110 through bearings 116 and also through bearings 118 to shaft 108. This allows the first section 12 to freely rotate relative to the shafts 108 and 110 and relative to the drive section 16. The first section is appropriately guided in a 45° helical rotation with first section guide wheels 96. The second section 14 is rotationally coupled to an end 120 of shaft 108 as through a bearing 122, so that both the first section 12 and the second section 14 are driven linearly along the pipeline 8 by drive section 16. Each section is substantially free to bend relative to the other sections at U-joints 112, 114 and also 124 so that pipelines having a certain amount of curvature can be traversed without binding. U-joint 124 couples the second section angled drive wheels 98 to the second plurality of flux generator and flux sensor units 56. Thus, not only do wheels 96 and wheels 98 cause helical rotation in an amount defined by the respective opposite angles of contact of wheels 96 and 98, but also the relative rotation between first section 12 and second section 14 is precisely maintained through gear mechanism 100. Gear mechanism 100 might be a planetary type gear system, which synchronizes the first section 12 in counter-rotation with the second section 14. Gear mechanism 100 is maintained in a fixed position relative to drive section 16, which drive section 16 is longitudinally aligned along the pipeline by guide wheels 20.

FIG. 4 is another alternative embodiment in which there are elongated magnetic flux generating magnets 126 and 128 with a plurality of sensors 130 and 132 interposed between helically shaped north and south poles 134 and 136 of the first section 12 and 138 and 140 of the second section 14. In this embodiment, a single elongated flux generator may be used in each section to provide complete coverage of the pipeline upon counter-rotation of the first and second sections at opposite 45° angles helically through the pipeline.

FIG. 5 depicts another alternative embodiment of the invention in which first and second counter-directional angular magnetic flux field generators and sensor units 142 and 144, respectively, are provided through a unique positioning of north contact poles 146 and 148 and south contact poles 150 and 152 on first and second flux generating and sensing units 142 and 144, respectively. The first and second units 142 and 144 need not rotate with respect to each other as an angular flux field is created which simply moves along the pipe based upon the appropriate spaced apart orientation of the north and south contact poles of each flux generator. A 45° helical angle exists between the respective north and south contact poles. A plurality of sensors 154 and 156 are positioned interposed between each north and south contact pole along a line corresponding to the helical 45° angle. Thus, a plurality of magnetic flux sensors 154 are evenly spaced and aligned with the predominant flux field generated between the north and south contact poles 146 and 150 of the first section 142. On the second section 146, the contact poles 148 and 152 are oriented in an opposite angular direction, such that if the north poles 146 are forward of the south poles 150 in the first section 142, then the south poles 152 of the second section will be longitudinally aligned with the south poles 150 of the first section 142 and the south poles 150 will be forward of the north poles 148 of the second section. The north poles 148 of the second section 144 will be aligned with the north poles 146 of the first section 142. In this manner, the first and second sections need not be rotated relative to each other, but rather are maintained at precisely the same location and preferably moved straight along the pipeline without any rotation.

In the embodiment described and depicted in FIG. 5, the distance between the sensors which are closest to the south poles is smaller than the distance between corresponding sensors closest to the north poles. The corresponding signals from each of the plurality of sensors can be superimposed one upon the other based upon the rate of travel of the pig and the distance between the corresponding sensors of each section. Thus, coordination of the sensory data for forming an overlapping signal pattern requires that the differences in the distances be appropriately accommodated.

A potential drawback for having fixed position magnets is that the area along the pipe at which the poles contact the pipe surface is not subject to detection with any of the incremental sensors 154 or 156 between the poles. Thus, in another alternative embodiment, two pairs of first and second sections may be used. The first pair would be offset from the second pair a radial distance corresponding to one-half of the circumferential spacing between the north and south poles of each pair. The first and second sections need not be rotated with respect to each other in this alternative embodiment, but rather are maintained in a fixed relationship with respect to each other, so that complete coverage of the internal pipeline surface is accomplished.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. An inspection pig, for inspecting an installed pipeline, comprising:

(a) a drive section;

(b) a first field generator and first sensor section connected to said drive section and driven thereby helically through the pipeline in a first rotational direction;

(c) a second field generator and second sensor section connected to said drive section and driven thereby helically through said pipeline in a second rotational direction counter to said first rotational direction; and (d) at least one electronic section operatively communicating with said first field generator and sensor section and said second field generator and sensor section for receiving and recording field interruption sensory data from said first and second field generator and sensor sections and from which sensory data a plot of anomalies in the pipeline can be generated as a grid representing sensory data along intersecting helical pathways of said first and second field generator and sensor sections.

2. A pipeline inspection pig as in claim 1 wherein said at least one electronic section data recorder comprises first and second electronic sections, each including a signal receiving and data storage device for recording data received from said first and second sensor sections, respectively.

3. A pipeline inspection pig as in claim 1 wherein said at least one electronic section further comprises a continuous on-board plotter.

4. A pipeline inspection pig as in claim 1 wherein said at least one electronic section further comprises a remote above-ground computer for receiving signals from said sensors while said pipeline inspection pig is in the pipeline.

5. A pipeline inspection pig as in claim 1 further comprising:

(a) a pressure boot attached around said drive section of said inspection pig for sliding contact with an interior wall of the pipeline so that said pig is moved linearly through the pipeline with differential pressure caused by fluid flowing in the pipeline, which booted drive section is rotationally interconnected to said first and second field generator and sensor sections so that said first and second field generator and sensor sections can rotate relative to said booted drive section of said inspection pig;

(b) a first rotation mechanism attached to said first field generator and sensor section for rotating said first generator and sensor section in one direction relative to said booted drive section as said inspection pig moves linearly through the pipeline; and (c) a second rotational mechanism attached to said second field generator and sensor section for rotating said second generator and sensor section relative to said booted drive section of said inspection pig in a rotational direction opposite from said direction of rotation of said first section.

6. A pipeline inspection pig as in claim 5 wherein said booted drive section further includes a plurality of wheels attached to said inspection pig directed coaxially with and contacting the interior pipeline surface with radial tension for centering said drive section and said plurality of wheels each having a rotational axis perpendicular to the pipeline axis so that said booted drive section moves linearly along the pipeline without rotation.

7. A pipeline inspection pig as in claim 6 wherein said at least one drive section comprises a front drive section and a rear drive section.

8. A pipeline inspection pig as in claim 6 further comprising means for monitoring a linear position of said inspection pig along the pipeline.

9. A pipeline inspection pig as in claim 8 wherein said means for monitoring a linear position of said inspection pig along the pipeline comprises an odometer engaging the pipeline interior surface in nonslip rolling contact.

10. A pipeline inspection device as in claim 8 wherein said means for monitoring a linear position of said inspection pig along the pipeline comprises a linearly rigid axially flexible strand pulled by said inspection pig along the pipeline from an originating location by which a length of said strand which is pulled from an originating point is measurable so that a location of said inspection pig along the pipeline can be determined from the length of strand pulled thereinto.

11. A pipeline inspection pig as in claim 5 wherein:

(a) said first rotation mechanism comprises a first set of circumferentially spaced angled wheels attached to said first field generator and sensor section for angled rolling contact with the pipeline interior wall of the pipeline, each said angled wheel of said first set at a pre-set angular orientation so that said field generator and sensor section is spaced uniformly from the pipeline interior wall and is rotated at a first constant helical angle; and (b) said second rotation mechanism comprises a second set of circumferentially spaced angled wheels attached to said second field generator and sensor section for angled rolling contact with the pipeline interior wall of the pipeline, each said angled wheel of said second set at pre-set angular orientation so that said field generator and sensor section is spaced uniformly from the pipeline interior wall and is rotated at a second constant helical angle opposite from said first constant angle.

12. A pipeline inspection pig as in claim 11 wherein said first field generator and sensor section is interconnected with said second field generator and sensor section with a mechanical gear mechanism, such that each section is rotated synchronized with respect to the other in opposite directions.

13. A pipeline inspection pig as in claim 5 wherein:

(a) said first field generator and sensor section comprises a first plurality of north and south magnetic poles positioned around said inspection pig having said north poles and south poles contacting the interior surface of the pipeline at spaced apart locations at an angle corresponding to said first constant helical angle at which said first field generator is driven and rotated through the pipeline so that a first plurality of magnetic flux fields are produced in said pipeline between said first plurality of north and south poles; and (b) said second field generator and sensor section comprises a plurality of north and south magnetic poles positioned around said inspection pig having north and south poles contacting the pipeline interior surface at spaced apart locations at an angle corresponding to the helical angle at which said second field generator and sensor section is driven and rotated through said pipeline, so that a second plurality of magnetic flux fields are produced in said pipeline between said second plurality of north and south poles.

14. A pipeline inspection pig as in claim 13 wherein:

(a) said first field generator and sensor section further comprises a plurality of circumferentially spaced sensors, one or more of which is positioned between each of said plurality of north and south angled magnetic contact poles of said first field generator and sensor section; and (b) said second field generator and sensor section further comprises a plurality of circumferentially spaced sensors, one or more of which is positioned between each of said north and south angled magnetic contact poles of the second field generator and sensor section.

15. A pipeline inspection pig as in claim 5 wherein:

(a) said first field generator and sensor section comprises a single elongated first magnet having an elongated first north pole contacting the interior surface of the pipeline at a 45° helical angle, which elongated first north pole is sufficiently long to extend, at said 45° helical angle, 180° circumferentially around the inside of the pipeline, an elongated first south pole positioned at a 45° helical angle parallel to the first north pole and extending, at said 45° helical angle, 180° circumferentially around the pipeline with a constant spacing between the first north and the first south elongated contacting poles; and (b) said second field generator and sensor section comprises a single elongated second magnet having an elongated second north pole contacting the interior surface of the pipeline at a −45° helical angle, which elongated north pole is sufficiently long to extend, at said −45° helical angle, 180° circumferentially around the interior surface of the pipeline, and an elongated second south pole positioned at a −45° helical angle parallel to said second north pole of the second field generator and sensor and extending, at said −45° helical angle, halfway around the circumference of the pipeline.

16. A magnetic pipeline inspection vehicle with counter-rotating helical sensing sections for detection of lateral and circumferential flaws in walls of a pipeline, said inspection vehicle comprising:

(a) a drive mechanism;

(b) a first magnetic field generator section connected to said drive mechanism to be driven through said pipeline for producing a regular magnetic field in said pipeline walls;

(c) a first sensor section connected to said drive mechanism and cooperating with said first magnetic field generator section to be driven through said pipeline simultaneously laterally and rotationally in a first rotational direction to produce a constant angle helical motion and to sense irregularities in said regular magnetic field so that both lateral and circumferential flaws in said pipeline are detected;

(d) a second magnetic field generator section connected to said drive mechanism to be driven through said pipeline for producing a regular magnetic field in said pipeline walls; and (e) a second sensor section connected to said drive mechanism and cooperating with said first magnetic field generator section to be driven through said pipeline simultaneously laterally and rotationally in a second rotational direction opposite from said first rotational direction of said first sensor to produce a constant angle helical motion and to sense irregularities in said regular magnetic field so that both lateral and circumferential flaws in said pipeline are detected.

17. A magnetic pipeline inspection vehicle as in claim 16 further comprising a linear odometer by which the location of the pipeline inspection vehicle within the pipeline.

18. A magnetic pipeline inspection vehicle with counter-rotating helical sensing sections as in claim 16 further comprising a planetary gear system interconnecting the first and second magnetic field generator and sensor sections so that said counter-rotation is mechanically synchronized at a fixed relationship so that the counter-rotating helical pathways of each first and second sensor section are maintained at opposite angles with respect to each other.

19. A magnetic pipeline inspection vehicle as in claim 16 further comprising a data recorder operatively connected to said first sensor section and said second section and said odometer for recording field interruption data corresponding to each sensor in the sensor sections for which a plot of anomalies in the pipeline can be generated as a grid of intersecting helical pathways of said first and second sensors.

20. A magnetic pipeline inspection vehicle as in claim 19 wherein said recorded data further includes recordation of position data from said odometer and further includes a data processor for superimposing the first and second sensor data on a location coordinated grid of intersecting helical pathways of said first and second sensors.

* * * * *

UNITED STATES PATENT AND TRADEMARK OFFICE
CERTIFICATE OF CORRECTION

PATENT NO. : 5,454,276
DATED : October 3, 1995
INVENTOR(S) : Wernicke, Timothy K.

It is certified that error appears in the above-indentified patent and that said Letters Patent is hereby corrected as shown below:

IN THE DRAWINGS:

The shafts which couple the four differential bevel gears in the Mechanical Gear Mechanism 100, should be cross coupled in the shape of a "+", and the End 120 of Shaft 108 should include a retaining shoulder, as depicted and shown in Replacement Drawing Fig. 3, Sheet 2 of 3, attached hereto.

FIG. 3

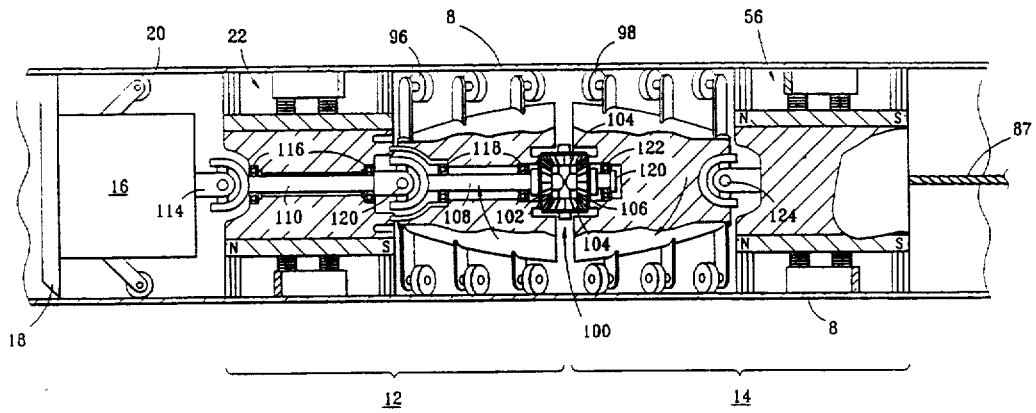

Signed and Sealed this

Thirteenth Day of August, 1996

Attest:

BRUCE LEHMAN

Attesting Officer

Commissioner of Patents and Trademarks